United States Patent [19]

Hisamitsu et al.

[11] Patent Number: 4,680,403
[45] Date of Patent: Jul. 14, 1987

[54] PROCESS FOR PRODUCING N-PROTECTED-α-L-ASPARTYL-L-PHENYLALANINE METHYL ESTER

[75] Inventors: Kunio Hisamitsu, Funabashi; Tadashi Takemoto, Kawasaki; Toyoto Hijiya, Yokosuka; Satoji Takahashi, Yokkaichi, all of Japan

[73] Assignee: Ajinomoto Co., Inc., Tokyo, Japan

[21] Appl. No.: 806,811

[22] Filed: Dec. 10, 1985

[30] Foreign Application Priority Data

Jan. 17, 1985 [JP] Japan .................................. 60-6304

[51] Int. Cl.$^4$ .......................................... C07D 307/22
[52] U.S. Cl. ................................... 546/247; 548/478; 549/273; 549/477; 560/38; 562/445; 562/571; 426/548
[58] Field of Search .................. 260/998.21; 546/247; 426/548; 548/478; 549/477, 253; 560/38; 562/571, 445

[56] References Cited

U.S. PATENT DOCUMENTS 3,786,039  1/1974  Ariyoshi et al. ............... 260/998.21
3,833,553  9/1974  Ariyoshi et al. ............... 260/998.21
4,550,180 10/1985  Takemoto et al. .................. 549/253

Primary Examiner—John Kight
Assistant Examiner—Nathan M. Nutter
Attorney, Agent, or Firm—Oblon, Fisher, Spivak, McClelland & Maier

[57] ABSTRACT

The invention relates to a process for producing N-protected-α-L-aspartyl-L-phenylalanine methyl ester, which comprises esterifying L-phenylalanine with methanol in the presence of a strong acid catalyst, adding, to the resulting solution, an aqueous alkaline solution to neutralize the acid catalyst and a water-immiscible organic solvent to extract the free L-phenylalanine methyl ester thus formed, collecting the organic layer, and reacting the L-phenylalanine methyl ester dissolved in said collected organic layer with N-protected-L-aspartic anhydride.

8 Claims, No Drawings

PROCESS FOR PRODUCING N-PROTECTED-α-L-ASPARTYL-L-PHENYLALANINE METHYL ESTER

DETAILED DESCRIPTION OF THE INVENTION

This invention relates to a process for producing N-protected-α-L-aspartyl-L-phenylalanine methyl ester (N-protected-α-APM). More particularly, it relates to a process for producing N-protected-α-APM which comprises esterifying L-phenylalanine (L-Phe) with methanol in the presence of a strong acid (such as sulfuric acid and hydrogen chloride) as catalyst, adding, to the resulting solution, an aqueous alkaline solution to neutralize the acid catalyst and a water-immiscible organic solvent to extract the free L-phenylalanine methyl ester (PM), collecting the organic layer, and reacting the PM dissolved in said collected organic layer with N-protected-L-aspartic anhydride (N-protected-Asp⊃O). This invention further relates to an improvement to the above claimed process, wherein part or all of the methanol is removed from said collected organic layer, prior to the reaction with N-protected-Asp⊃O.

The N-protected-α-APM obtained by the process of this invention can be easily converted, by removal of the N-protective group by usual methods, into aspartame (α-L-aspartyl-L-phenylalanine methyl ester) which is receiving attention as a new sweetener having sucrose-like sweetness.

The N-protective group may be benzyloxycarbonyl (Z), formyl (F), 1-methyl-2-acetylvinyl (K) or other protective group commonly employed in peptide chemistry.

In the synthesis of N-protected-α-APM by condensation between PM and N-protected-Asp⊃O, PM is used normally in the form of hydrochloride. Typical examples include a method in which a suspension of PM hydrochloride in an organic solvent is neutralized with an organic base (preferably triethylamine) to give free PM, the salt formed by neutralization is removed, and the free PM dissolved in the solvent is then allowed to react with N-protected-Asp⊃O; and a process in which a suspension of PM hydrochloride in a mixture of water and an organic solvent is neutralized with an inorganic base (preferably sodium carbonate), thereby transferring the free PM formed by neutralization into organic layer, followed by reaction with N-protected-Asp⊃O in the organic medium (U.S. Pat. No. 3,786,039).

These methods employ PM hydrochloride as starting material, which must be previously isolated after esterification of L-Phe with methanol in the presence of hydrogen chloride. This is not advantageous for industrial application because of the low overall yield and the added reaction step.

For commercial production, it would be advantageous to suspend L-Phe in methanol, esterify it by the action of a strong acid such as sulfuric acid hydrogen chloride, add an aqueous alkaline solution and an organic solvent sparingly soluble in water in order to neutralize the acid catalyst and to transfer the free PM into the organic layer, and react the PM dissolved in said organic layer with N-protected-Asp⊃O, because there is no need for the step of isolating PM hydrochloride or sulfate. However, the condensation yield is still not high even with this method.

We have discovered that removal of methanol from the organic layer containing PM prior to rection with N-protected-αAsp⊃O minimizes decomposition of the anhydride in the subsequent step, thereby enhancing the yield of N-protected-αAPM.

In this invention methyl esterification of L-Phe may be effected by any known method, for example, by the Fischer process in which hydrogen chloride gas is introduced to a suspension of L-Phe in methanol, or by addition of conc. sulfuric acid to a suspension of L-Phe in methanol. In this reaction, more than equimolar amount of methanol (normally more than six molar proportions based on L-Phe) should be used because it serves as both reactant and reaction medium.

The alkaline substance used to neutralize the esterified solution may be selected from inorganic bases, such as sodium carbonate, sodium bicarbonate and sodium hydroxide, or organic bases such as triethylamine and pyridine. These should preferably be added to the reaction solution in the form of an aqueous solution.

The amount of alkali to be used must be at least equimolar based on the strong acid (e.g., sulfuric acid and hydrogen chloride) present in the system, and is normally one to two molar proportions, because use of an excessive amount tends to cause hydrolysis of the ester. There is no specific limitation upon the concentration of alkali in aqueous solution; however, 1 to 15% solution is normally used because a higher concentration causes the salt formed by neutralization to precipitate, making neutralization and extraction operations difficult, and because lower concentrations increase the amount of PM left dissolved in the aqueous layer, resulting in lower product yields.

The organic solvent used to extract PM may be any solvent that is immiscible with water, but acetates such as methyl acetate and ethyl acetate, hydrocarbons such as toluene, xylene, hexane and cyclohexane, and halogenated hydrocarbons such as chloroform, dichloromethane and ethylene dichloride are advantageously employed.

There is no specific limitation upon the order of adding the neutralizer solution and the organic solvent. These may be added in any way so long as it ensures efficient neutralization of the acid catalyst and complete separation of the resulting mixture into two layers: aqueous layer and organic layer containing PM.

No special technique is needed to separate the PM-containing organic solution from the esterification reaction mixture to which an aqueous alkaline solution and a water-immiscible organic solvent have been added; this can be done, for example, by shaking or agitating the reaction mixture for 5 to 30 minutes, followed by settling until two layers become clearly separated.

During this operation, most of the excess methanol is transferred to the aqueous layer, with part of it being moved to the organic layer. Thus the PM-containing organic layer contains some methanol, its concentration ranging from 0.4 to 10 g/dl.

Removal of this methanol from the PM-containing organic solution may be effected by concentration of the solution or by extraction with water, but the former is preferred in terms of product yield and ease of operation.

The suitable conditions for removing methanol by concentration vary with the type of solvent used for PM extraction, and are normally at a temperature not higher than 90° C. under a reduced pressure of 10 to 760

Torr. However concentration at a temperature below 60° C. is preferable to avoid decomposition of PM.

In connection with the degree of methanol removal from the PM-containing organic solution, we have discovered that the yield of N-protected-α-APM increases with decreasing amount of methanol present in the reaction system.

When the N-protective group is F-group, for example, the yield of N-formyl-α-L-aspartyl-L-phenylalanine methyl ester (F-α-APM) can be enhanced by 15% by removing methanol from the PM-containing solution prior to its reaction with N-protected-Asp⊃O. A detailed study showed that the concentration of methanol in the PM-containing solution should preferably be reduced below 0.25 g/dl in this particular case.

When the N-protective group is Z, the yield of N-benzyloxycarbonyl-α-L-aspartyl-L-phenylalanine methyl ester (Z-α-APM) can be enhanced by 7% by removal of methanol. The methanol concentration should preferably be reduced below 0.25 g/dl in this case too.

When the N-protective group is K-group, the product yield can be enhanced by 6%. It is preferable to reduce the methanol concentration down to 0.25 g/dl or lower.

Reaction of the PM dissolved in organic solvent (containing or not containing methanol) with N-protected-Asp⊃O may be effected by any known process or by any method obvious from prior arts (U.S. Pat. No. 3,786,039).

N-Protected-α-APM thus obtained can be easily converted to α-L-aspartyl-L-phenylalanine methyl ester (α-APM) by removal of the protective group.

Thus the process of this invention achieves significantly enhanced yeild of N-protected-αAPM, and therefore of α-L-aspartyl-L-phenylalanine methyl ester (α-APM). In addition, this process simplifies the separation and purification steps, and is very advantageous for commercial production of α-APM.

The following examples are intended only to further illustrate the invention but are not to be considered to limit its scope.

EXAMPLE 1

(1) To a suspension of 16.5 g L-Phe in 40 ml methanol, was added 8 ml of 98% sulfuric acid, and the reaction was continued at 85° C. for four hours. Toluene (210 ml) and 10% aqueous solution of sodium carbonate (80 ml) were then added, and the mixture was stirred for 30 minutes and allowed to stand, giving 227 ml of toluene solution. This solution contained 0.091 mole of PM and 0.80 g/dl methanol.

(2) To a suspension of 13.2 g (0.091 mole) of N-formyl-L-aspartic anhydride (F-Asp⊃O) in 19 ml acetic acid was added the tolulene solution of PM prepared in (1) above, and the reaction was continued at room temperature for 1.5 hours. Analysis of this reaction mixture by high-performance liquid chromatography (HPLC) showed formation of F-α-APM in 65% yield based on PM.

EXAMPLE 2

A PM-containing toluene solution obtained in the same way as in step (1) of Example 1 was concentrated at 60° C. under reduced pressure to a volume of 200 ml, giving a PM-containing solution with a methanol concentration below 0.001 g/dl.

Similarly, PM-containing toluene solutions with methanol concentrations of 0.25 g/dl and 0.50 g/dl were prepared.

Each of these toluene solutions was allowed to react with F-Asp⊃O in the same manner as in step (2) of Example 1. Analysis revealed formation of F-α-APM in 80%, 79% and 72% yields, respectively, based on PM.

EXAMPLE 3

To a suspension of 16.0 g N-benzyloxycarbonyl-L-aspartic acid (Z-Asp) in 24 ml toluene, was added 7.7 g of acetic anhydride, and the reaction was continued at room temperature for six hours to form N-benzyloxycarbonyl-L-aspartic anhydride (Z-Asp⊃O).

A PM-containing toluene solution prepared in the same way as in step (1) of Example 1 was added to the suspension of the anhydride (Z-Asp⊃O) obtained above, and the reaction was continued at room temperature for 1.5 hours. HPLC analysis showed formation of Z-α-APM in 75% yield.

EXAMPLE 4

Three toluene solutions containing PM were prepared in the same way as in step (1) of Example 1, which were concentrated so as to give solutions with methanol contents of below 0.001 g/dl, 0.25 g/dl and 0.43 g/dl, respectively.

Each of the toluene solutions thus prepared was allowed to react with Z-Asp⊃O in the same manner as in Example 3, giving Z-α-APM in 82%, 80% and 77% yields, respectively, based on PM.

EXAMPLE 5

(1) Hydrogen chloride gas (13 g) was introduced into a suspension of 19.9 g L-Phe in 50 ml methanol with stirring, and the reaction mixture was allowed to stand at room temperature for two days. Ethyl acetate (380 ml) and 10% aqueous solution of sodium carbonate (180 ml) were added, and the mixture was shaken for 30 minutes and then allowed to stand, giving 445 ml of PM-containing ethyl acetate solution. This contained 0.112 mole PM and 3.5 g/dl methanol.

(2) A mixture of 26 g disodium N-(1-methyl-2-acetylvinyl)-L-aspartate (K-Asp.Na$_2$), 50 ml ethyl acetate and 22 ml acetic acid was cooled to −20° C. with stirring, 12.5 g acetic anhydride was added, and the mixture was stirred overnight.

After heating this solution to 40° C., the ethyl acetate solution of PM prepared in step (1) above was added, and the reaction was continued for 30 minutes. 1N-HCl (100 ml) was then added, and the mixture was stirred for one hour and allowed to stand until two layers become clearly separated.

Analysis of α-APM in the aqueous layer with an automatic amino acid analyzer (column: 9φ×100 mm; packings: Hitachi 2611 resin) showed its formation in 50% yield based on K-Asp.Na$_2$.

(3) A PM-containing ethyl acetate solution prepared in the same way as in (1) above was concentrated at 55° C. under reduced pressure to a volume of 400 ml. The solution thus obtained contained practically no methanol (only below 0.001 g/dl). Reaction of this solution in a similar manner to that in step (2) above gave α-APM in 65% yield.

(4) Two ethyl acetate solutions containing PM were prepared in the same way as in step (1) above, and concentrated at 55° C. under reduced pressure until the methanol concentration fell to 0.80 g/dl and 0.25 g/dl, respectively. Reaction of these solutions in the same manner as in step (2) above gave α-APM in 59% and 64% yields, respectively.

What is claimed is:

1. A process for producing N-protected-α-L-aspartyl-L-phenylalanine methyl ester which comprises esterifying L-phenylalanine with methanol in the presence of a strong acid as catalyst, adding, to the resulting solution, an aqueous alkaline solution to neutralize the acid catalyst and a water-immiscible organic solvent to extract the free L-phenylalanine methyl ester thus formed, collecting the organic layer, and reacting the L-phenylalanine methyl ester dissolved in said collected organic layer with N-protected-L-aspartic anhydride.

2. The process for producing N-protected-α-L-aspartyl-L-phenylalanine methyl ester as defined in claim 1, wherein part or all of the methanol is removed from said collected organic layer prior to the reaction with N-protected-L-aspartic anhydride.

3. The process for producing N-protected-α-L-phenylalanine methyl ester as defined in claim 2, wherein the methanol concentration is reduced below 0.25 g/dl.

4. The process according to claim 1, wherein the N-protecting group is selected from the group consisting of benzyloxycarbonyl, formyl, and 1-methyl-2-acetylvinyl.

5. The process according to claim 1, wherein said aqueous alkaline solution is of sodium carbonate, sodium bicarbonate, sodium hydroxide, triethylamine, or pyridine.

6. The process according to claim 1, wherein said water-immiscible organic solvent is selected from the group consisting of methyl acetate, ethyl acetate, toluene, xylene, hexane, cyclohexane, chloroform, dichlormethane, and ethylenedichloride.

7. The process according to claim 2, wherein said methanol is removed by concentration of the solution or by extraction with water.

8. The method according to claim 7, wherein when said methanol is removed by concentration of the solution, said concentration is carried out at a temperature below 60° C. at a reduced pressure of from 10–760 Torr.

* * * * *